(12) United States Patent
Park et al.

(10) Patent No.: US 10,973,940 B2
(45) Date of Patent: Apr. 13, 2021

(54) COMPOSITION FOR PREVENTING ODOR, CONTAINING ODORLESS MICROORGANISMS

(71) Applicant: Hyundai Motor Company, Seoul (KR)

(72) Inventors: So Yoon Park, Gyeonggi-do (KR); Tae Hee Lee, Gyeonggi-do (KR); Ji Wan Kim, Gyeonggi-do (KR); Ki Young Yoon, Seoul (KR)

(73) Assignee: Hyundai Motor Company, Seoul (KR)

( * ) Notice: Subject to any disclaimer, the term of this patent is extended or adjusted under 35 U.S.C. 154(b) by 66 days.

(21) Appl. No.: 16/021,570

(22) Filed: Jun. 28, 2018

(65) Prior Publication Data
US 2018/0303963 A1    Oct. 25, 2018

Related U.S. Application Data (63) Continuation of application No. PCT/KR2016/015473, filed on Dec. 29, 2016.

(30) Foreign Application Priority Data

| Dec. 29, 2015 | (KR) | 10-2015-0188550 |
| Dec. 29, 2015 | (KR) | 10-2015-0188601 |
| Dec. 29, 2015 | (KR) | 10-2015-0188609 |
| Dec. 29, 2015 | (KR) | 10-2015-0188615 |

(51) Int. Cl.

| A61L 9/01 | (2006.01) |
| C12N 1/20 | (2006.01) |
| C12R 1/01 | (2006.01) |
| B60H 3/00 | (2006.01) |
| B60H 1/00 | (2006.01) |
| B01D 53/85 | (2006.01) |
| B01D 53/84 | (2006.01) |
| F25B 39/02 | (2006.01) |

(52) U.S. Cl.
CPC .............. *A61L 9/01* (2013.01); *B01D 53/84* (2013.01); *B01D 53/85* (2013.01); *B60H 1/00335* (2013.01); *B60H 3/0092* (2013.01); *C12N 1/20* (2013.01); *C12R 1/01* (2013.01); *B01D 2251/95* (2013.01); *B01D 2257/90* (2013.01); *B01D 2257/91* (2013.01); *F25B 39/02* (2013.01); *Y02A 50/20* (2018.01)

(58) Field of Classification Search
CPC .......... A61L 9/01; B01D 53/85; B01D 53/84; B01D 2257/90; B01D 2257/91; B01D 2251/95; B60H 1/00335; B60H 3/0092; C12R 1/01; C12N 1/20; Y02A 50/2358; F25B 39/02
See application file for complete search history.

(56) References Cited

U.S. PATENT DOCUMENTS

| 2007/0205148 A1 | 9/2007 | Jones et al. |
| 2007/0207534 A1 | 9/2007 | Jones et al. |
| 2011/0233125 A1 | 9/2011 | Jones et al. |
| 2015/0125417 A1 | 5/2015 | McHatton et al. |
| 2015/0337257 A1 | 11/2015 | Kim et al. |
| 2015/0353399 A1 | 12/2015 | Wackett et al. |
| 2019/0216965 A1* | 7/2019 | Kim .......................... A61L 9/00 |

FOREIGN PATENT DOCUMENTS

| CN | 1300318 A | 6/2001 |
| CN | 103124566 A | 5/2013 |
| CN | 103476921 A | 12/2013 |
| CN | 103961735 A | 8/2014 |
| CN | 105264063 A | 1/2016 |
| EP | 1077252 A1 | 2/2001 |
| EP | 2 937 414 A1 | 10/2015 |
| EP | 3456361 A1 | 3/2019 |
| KR | 10-2012-0020309 | 3/2012 |
| KR | 10-2015-0058125 | 5/2015 |
| KR | 10-2015-0105637 | 9/2015 |
| KR | 1020150126325 A | 11/2015 |
| KR | 1020150126326 A | 11/2015 |
| RU | 2414508 C2 | 3/2011 |
| WO | 2014/098543 A1 | 6/2014 |

OTHER PUBLICATIONS

Kato, Y. et al., Methylobacterium persicinum, Methylobacterium komagatae, Methylobacterium brachiatum, Methylobacterium tardum and Methylobacterium gregans, isolated from Freshwater, 2008, International Journal of Systematic and Evolutionary Microbiology, 58, 1134-1141 (Year: 2008).*
Bowers, L., et al., Studies on a strain of Caulobacter from water. I. Isolation and identification as Caulobacter vibrioides, 1954, 68(2), 194-200 (Year: 1954).*
Delamuta, J., et al., Polyphasic evidence supporting the reclassification of Bradyrhizobium japonicum group Ia strains as *Bradyrhizobium diazoefficiens* sp. nov., 2013, International Journal of Systematic and Evolutionary Microbiology, 63, 3342-3351 (Year: 2013).*
Simmons, R. B. et al., The Occurrence and Persistence of Mixed Biofilms in Automobile Air Conditioning Systems, 1999, Current Microbiology, 39, 141-145 (Year: 1999).*

(Continued)

*Primary Examiner* — Louise W Humphrey
*Assistant Examiner* — Anjali Ajit Hirani
(74) *Attorney, Agent, or Firm* — Mintz Levin Cohn Ferris Glovsky and Popeo, P.C.; Peter F. Corless (57) ABSTRACT

Disclosed is a coating composition for preventing odor. The coating composition may include one or more types of odorless microorganisms selected from the group consisting of *Caulobacter vibrioides, Bradyrhizobium diazoefficiens, Bradyrhizobium daqingense* and *Methylobacterium brachiatum* or a culture solution thereof. Further provided is a method for preventing odor, and the method may include applying the coating composition for preventing odor. When a biofilm is formed from the microorganisms in the coating composition by coating an object on which an odor-causing microorganism can live, the inflow and the inhabitation of external microorganisms generating odor may be significantly blocked, thereby enabling odor to be effectively prevented.

16 Claims, 3 Drawing Sheets

(56) References Cited

OTHER PUBLICATIONS

Simmons et al., "The Occurrence and Persistence of Mixed Biofilms in Automobile Air Conditioning Systems", Current Microbiology, vol. 39, (1999), pp. 141-145.
Baek, Evaluation of Microbes Through Biological Activated Carbon & Microfiltration Within Water Treatment Processes, Yonsei Graduate School, Department of Biomedical Laboratory Science, Master's Thesis, Jan. 16, 2015, <URL: http://www.riss.kr/link?id=T13775767>.
International Search Report dated Apr. 7, 2017 in corresponding PCT Application No. PCT/KR2016/015478.

* cited by examiner

COMPOSITION FOR PREVENTING ODOR, CONTAINING ODORLESS MICROORGANISMS

CROSS REFERENCES TO RELATED APPLICATIONS

This Application is a Continuation of Application PCT/KR16/015473 filed on Dec. 29, 2016 which claims priority from Application 10-2015-0188550 filed on Dec. 29, 2015 in the Republic of Korea; which claims priority from Application 10-2015-0188615 filed on Dec. 29, 2015 in the Republic of Korea; which claims priority from Application 10-2015-0188609 filed on Dec. 29, 2015 in the Republic of Korea which claims priority from Application 10-2015-0188601 filed on Dec. 29, 2015 in the Republic of Korea. The entire contents of these applications are incorporated herein by reference in their entirety.

TECHNICAL FIELD

The present disclosure relates to a composition or a coating composition for preventing odors including at least one odorless microorganism selected from the group consisting of *Caulobacter vibrioides, Bradyrhizobium diazoefficiens, Bradyrhizobium daqingense* and *Methylobacterium brachiatum*, or a culture solution thereof and a method for preventing odors using the same.

BACKGROUND

Clean air is recognized as essential to human health and well-being, and offensive odors or contaminated air may disturb the pleasant environment. For example, quality of unsatisfactory indoor air in closed conditions may be determined by the following factors: indoor air contamination that is generated directly from the material constituting the enclosed environment (building, vehicle, and the like), air pollution which is caused by human activity or a substance introduced from the outside.

Air conditioning systems are systems that reduce the indoor temperature and optimize the indoor environment, for air conditioning including conditioning the temperature, humidity, airflow and cleanliness of the air in buildings, vehicles, trains, ships, aircraft, and the like. These air conditioning systems have been used increasingly with improvement in standards of living. However, although the air conditioning systems has brought about a great development in basic functions, many environmental issues to improve the quality of indoor air remain unsolved.

Although the cause of odor of air conditioners among air conditioning systems is known to be metabolites of fungi and bacteria, there is no specific report regarding the types of fungi and bacteria and amounts of metabolites secreted by these microorganisms.

The air conditioning system may have a structure where all air passing through the blower passes through the evaporator core (eva core). When heat exchange is carried out between cold refrigerant and air, water may condense on the surface of the evaporator core due to temperature difference. The continuous condensation of condensate water provides the environment for the growth or proliferation of fungi and bacteria. When fungi and bacteria proliferate in the evaporator core exposed to outside air, volatile organic compounds (mVOCs) of microorganisms may be produced from metabolites of bacteria perforated on the surface of the evaporator core. When the air passing through the evaporator core is blown into the room, the room may be exposed to odor of fungi and bacteria upon use for a long time due to volatile organic compounds produced by microorganisms.

The surface of the evaporator core where odors are emitted may be covered with a biofilm as the air conditioning system is used for a long period of time. For example, the biofilms are composed of bacteria, cell clusters and extracellular polymeric substance (EPS). EPS contains a variety of ingredients including proteins, polysaccharides, polyuronic acids, nucleic acids, lipids and the like. On the surface of the evaporator core, a variety of bacteria and fungi proliferate using biofilms as nutrients to release organic compounds (mVOCs) as metabolites by microorganisms. At this time, the odor emitted from the organic compounds (mVOCs) may produce offensive odor of air conditioners.

Various types of fragrances may be used to remove offensive odor are commercially available, but they cannot fundamentally remove fungi and bacteria growing in the evaporator core, and merely serve to temporarily relieve unpleasant odor. Currently commercially available antimicrobial agents have been used against common pathogens, but specific antimicrobial agents have not been developed to target certain fungi or bacteria in the air conditioning system.

In the related arts, a method of manufacturing an evaporator core including coating the surface of the evaporator core with a biofilm made of a certain odorless or fragrant microorganism has been reported in order to prevent deposition or proliferation of bacteria or fungi emitting an odor on the surface of the evaporator core. However, because these bacteria are not odorless microorganisms, effects, for example, whether or not the bacteria can survive on the evaporator core when coating the evaporator core therewith, or whether or not growth of microorganisms inducing odors such as unpleasant odors or odors can be prevented, are not sufficiently demonstrated.

The above description of the background art is intended only to improve understanding of the background of the present disclosure and should not be construed as recognizing that the above-described technologies are known to those having ordinary skill in the technical field to which the present disclosure pertains.

SUMMARY OF THE INVENTION

In preferred aspects, the present disclosure provides methods of effectively controlling odor-generating microorganisms using odorless microorganisms. For example, four species of microorganisms which do not generate odors in an air conditioning system were isolated. Accordingly, when forming a biofilm with these microorganisms or a combination thereof, growth of microorganisms emitting an offensive odor may be prevented and, as a result, generation of an offensive odor may be prevented.

The term "biofilm" as used herein refers to an aggregate of bacterial microorganisms in which bacterial cells adhere to each other and/or to a surface. These adherent cells are often covered with a matrix of extracellular polymeric substance (EPS), which is produced by the cells and/or host. Biofilm EPS has been characterized as composed of extracellular DNA, proteins, and polysaccharides. Such biofilms may form on any living or non-living surfaces, in particular both on solid surfaces as colonies and/or on liquid surfaces as pellicles.

In one aspect of the present disclosure, provided is a coating composition for preventing odors including at least one odorless microorganism selected from the group consisting of *Caulobacter vibrioides*, *Bradyrhizobium diazoefficiens*, *Bradyrhizobium daqingense*, and *Methylobacterium brachiatum*, or a culture solution thereof. The coating composition may suitably be applied to prevent odors in an air conditioning system.

Preferably, *Caulobacter vibrioides* may be *Caulobacter vibrioides* HKMC-14 (Accession number: KCCM 11685P), *Bradyrhizobium diazoefficiens* may be *Bradyrhizobium diazoefficiens* HKMC-15 (Accession number: KCCM 11686P), the *Bradyrhizobium daqingense* may be *Bradyrhizobium daqingense* HKMC-16 (Accession number: KCCM 11687P), and/or the *Methylobacterium brachiatum* may be *Methylobacterium brachiatum* HKMC-17 (Accession number: KCCM 11688P).

An optical density (O.D.) of the microorganism may suitably be of about 0.3 to 0.9.

In another aspect of the present disclosure, provided is an evaporator core coated with the coating composition as described herein for preventing odors.

Preferably, the microorganism as described herein may be adhered at a concentration of about $10^4$ cfu/g to $10^8$ cfu/g to the evaporator core.

The microorganism in the coating composition may suitably form a biofilm on a surface of the evaporator core.

Further provided is an air conditioning system that may include the evaporator core as described herein.

In another aspect of the present disclosure, provided is a method of manufacturing an odorless evaporator core which may not generate odors in an air conditioner. The method may include coating an evaporator core with the coating composition for preventing odors.

Preferably, the coating may include adhering microorganisms included in the composition at a concentration of about $10^4$ cfu/g to $10^8$ cfu/g to the evaporator core.

The method may further include proliferating microorganisms in the coated coating composition to form a biofilm.

The coating composition may suitably include *Caulobacter vibrioides* HKMC-14 (Accession number: KCCM 11685P) to prevent an odor in an air conditioning system. The coating composition may suitably include *Bradyrhizobium diazoefficiens* HKMC-15 (Accession number: KCCM 11686P) to prevent an odor in an air conditioning system. The coating composition may suitably include *Bradyrhizobium daqingense* HKMC-16 (Accession number: KCCM 11687P) to prevent an odor in an air conditioning system. The coating composition may suitably include *Methylobacterium brachiatum* HKMC-17 (Accession number: KCCM 11688P) to prevent an odor in an air conditioning system.

In another aspect of the present disclosure, provided is a method of preventing odors in an air conditioner. The method may include coating an evaporator core with the coating composition for preventing odors.

Preferably, the coating may include adhering microorganisms included in the composition at a concentration of about $10^4$ cfu/g to $10^8$ cfu/g to the evaporator core.

The method may further include proliferating microorganisms in the coated coating composition to form a biofilm.

Still further provided is a method of detecting odors in an air conditioner. The method may include coating an evaporator core with the coating composition for preventing odors. The method may further include feeding petroleum or an air contaminant serving as a nutrient source of microorganisms in the coated coating composition and detecting whether or not an odor is generated.

Also provided is *Caulobacter vibrioides* HKMC-14 (Accession number: KCCM 11685P) in the coating composition to prevent an odor in an air conditioning system. Provided is *Bradyrhizobium diazoefficiens* HKMC-15 (Accession number: KCCM 11686P) in the coating composition to prevent an odor in an air conditioning system. Provided is *Bradyrhizobium daqingense* HKMC-16 (Accession number: KCCM 11687P) in the coating composition to prevent an odor in an air conditioning system. Provided is *Methylobacterium brachiatum* HKMC-17 (Accession number: KCCM 11688P) in the coating composition to prevent an odor in an air conditioning system.

Still further provided is a vehicle that may include the evaporator core or the air conditioning system as described herein.

It is another object of the present disclosure to provide a method of providing an odorless microorganism for coating an evaporator core to prevent odors in an air conditioner.

Other aspects of the disclosure are disclosed infra.

DETAILED DESCRIPTION

Figure 1:
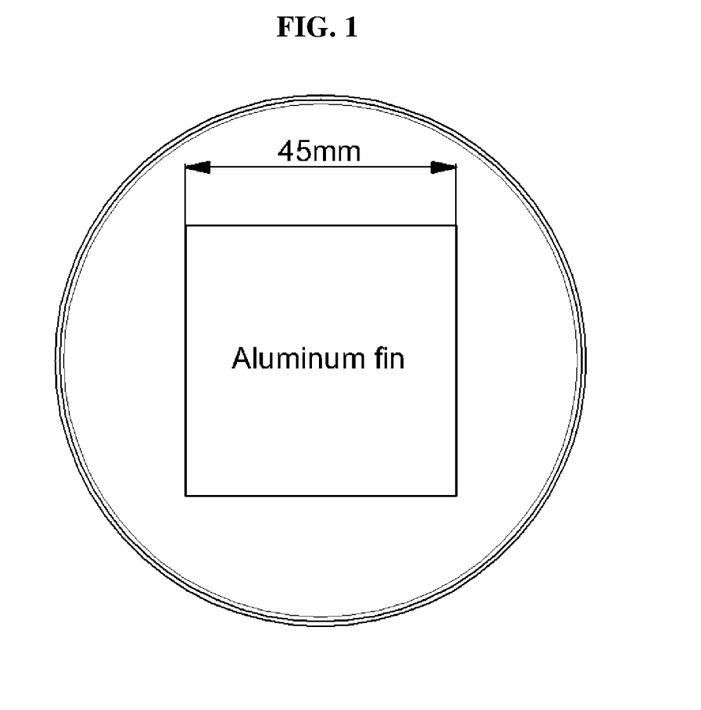
FIG. 1 shows an exemplary petri dish for seeding exemplary odorless microorganisms after sterilizing aluminum fins and dipping in a nutrient medium according to an exemplary embodiment of the present disclosure.
Figure 2:
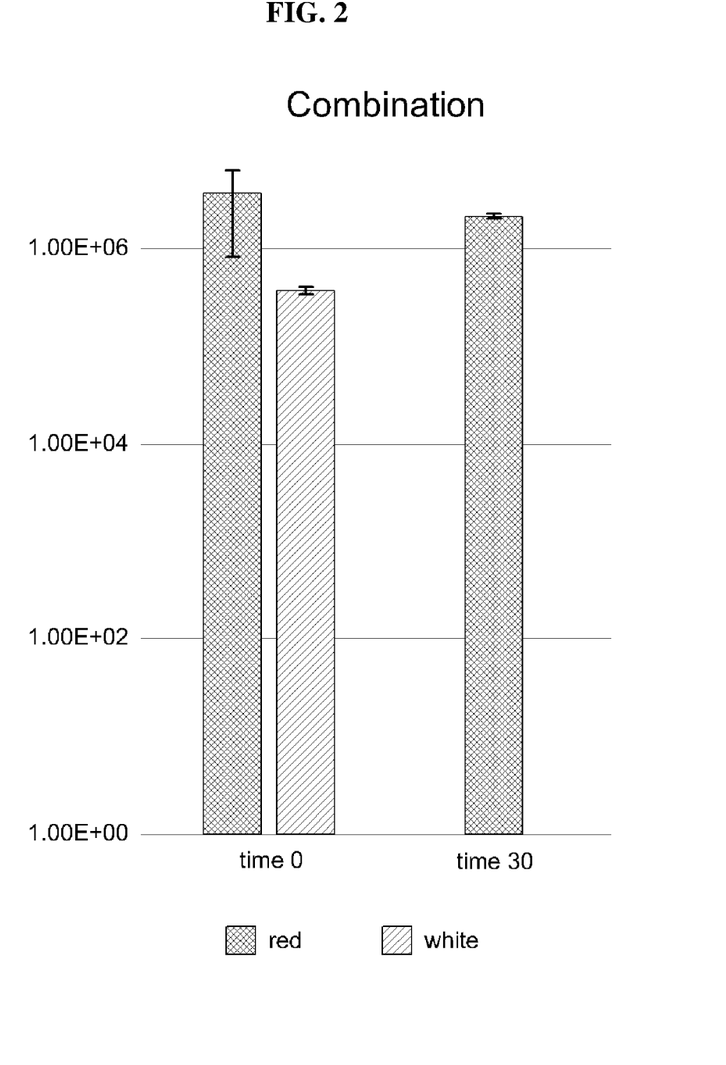
FIG. 2 shows the number of microorganisms depending on colony color for 30-day survival test combination (Example 9) of microorganisms isolated from samples from commercial taxi.
Figure 3:
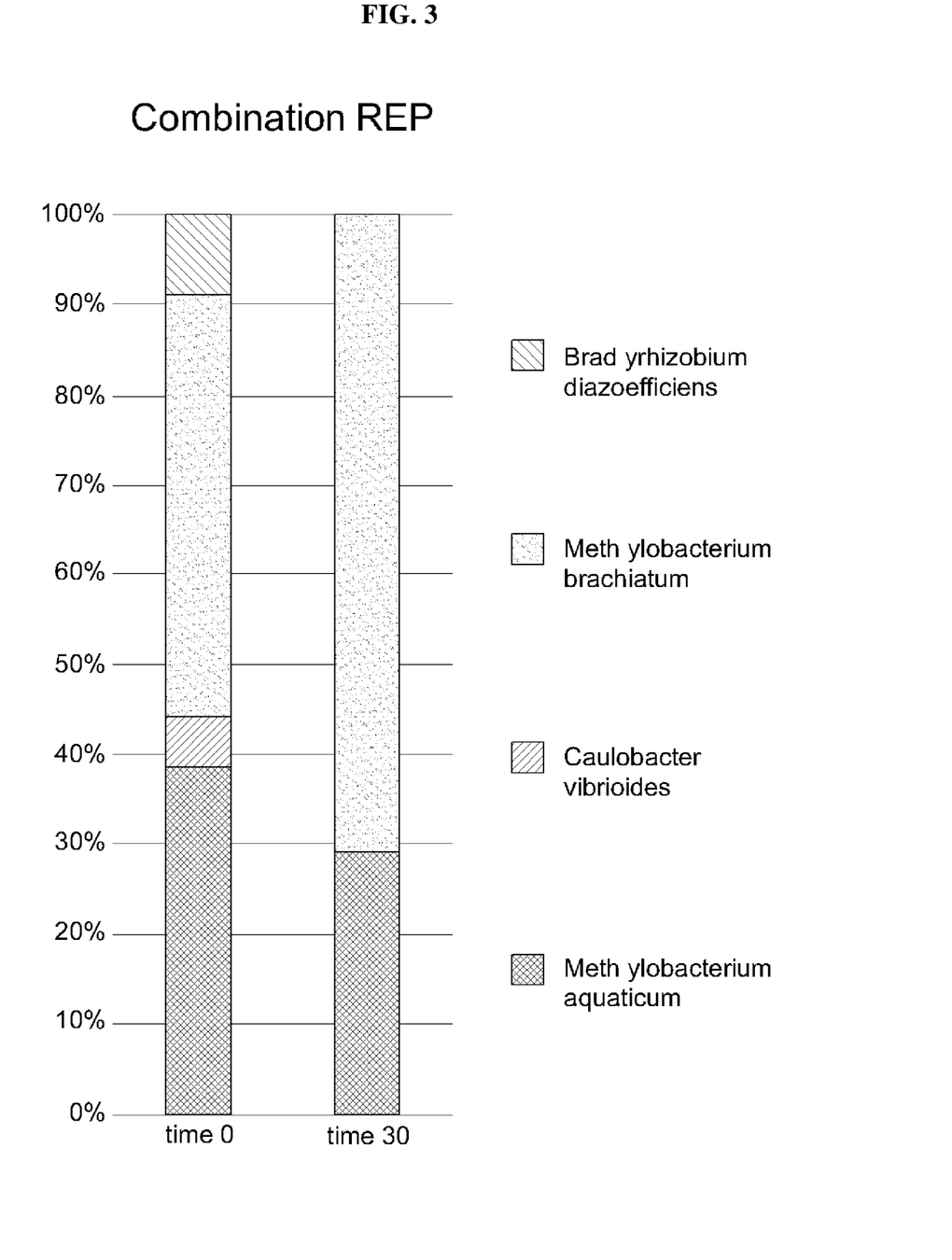
FIG. 3 shows the ratio of strains analyzed by REP-PCR for 30-day survival test combination (Example 9) of microorganisms isolated from eva core samples from commercial taxi.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, regions, integers, steps, operations, elements and/or components but do not preclude the presence or addition of one or more other features, regions, integers, steps, operations, elements, components, and/or combinations thereof.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

Further, unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, a detailed description will be given according to various exemplary embodiments of the present disclosure with reference to the appended drawings.

In one aspect, the present disclosure provides a coating composition for preventing odors including an odorless microorganism or a culture solution thereof.

The present inventors made attempts to find methods which are capable of effectively controlling microorganisms which induce odors using microorganisms, in particular, to fundamentally remove the cause of odors generated from an air conditioning system. As a result, they successfully isolated at least four species of microorganisms which do not generate odors in an air conditioning system. For example, when a biofilm is formed by these microorganisms or a combination thereof, growth of microorganisms emitting odors may be prevented and, as a result, generation of odors can be prevented.

As herein used, the term "air conditioning system" generically refers to a system which can maintain the temperature, humidity, cleanliness, flow or the like of air pleasant in an area, a part or entirety of which is isolated from an outdoor environment. Preferably, for example, the isolated area may be an indoor area, a part or the entirety of which is isolated from an outdoor environment, like the inside of a building or the inside of a vehicle, train, ship, aircraft or the like. Preferably, the air conditioning system is for example an air conditioner.

Based on the structure of the air conditioning system, all air having passed through a blower passes through the evaporator core, water continuously condenses on the surface of the evaporator core due to temperature difference, providing an environment which is optimal for growth of microorganisms. After a long time, a biofilm may be formed. The microorganisms in the evaporator may metabolize various indoor and outdoor materials as nutrients present in the air, generating odors derived from volatile organic compounds (mVOCs) produced as a result of metabolism.

Biofilms may be a form of microbial communities wherein microorganisms live as clusters, have a structure in which a layer is surrounded by one membrane, serve to protect microorganisms from the outside environment and provide nutrients. Exopolymeric substances (EPSs) may be present as an ingredient constituting the film and contain a variety of ingredients such as proteins, polysaccharides, polyuronic acids, nucleic acids, and lipids. On the surface of the evaporator core, various microorganisms may proliferate from the substances as nutrients and emit unpleasant odors from metabolites.

The present inventors isolated microorganisms which do not generate odors from the evaporator core and, as a result of culture of the microorganisms, separated and cultured dominant strains among microorganisms forming colonies. The method of separating and culturing dominant strains may be carried out using a variety of methods well-known to those skilled in the art. For example, dominant microorganisms may be selected through morphological approaches, such as dilution rate, and color, size or shape of colonies.

The isolated microorganism may include *Caulobacter, Bradyrhizobium*, or *Methylobacterium microorganism*, preferably *Caulobacter vibrioides, Bradyrhizobium diazoefficiens, Bradyrhizobium daqingense*, or *Methylobacterium brachiatum*.

The microorganisms were deposited at the Korea Culture Center of Microorganisms on Apr. 17, 2015 and were given the following accession numbers: *Caulobacter vibrioides* HKMC-14 (Accession number: KCCM 11685P), *Bradyrhizobium diazoefficiens* HKMC-15 (Accession number: KCCM 11686P), *Bradyrhizobium daqingense* HKMC-16 (Accession number: KCCM 11687P), and *Methylobacterium brachiatum* HKMC-17 (Accession number: KCCM 11688P).

The microorganism may be incorporated alone or as a combination thereof into the composition for preventing odors.

The coating composition (the "composition") for preventing odors according to the present disclosure may be used to prevent inhabitation of odor-inducing microorganisms and/or block odors thereof. For instance, the composition of the present disclosure may be coated on or sprayed onto the entirety or a part of odor-generating devices (for example, air conditioning systems, wastewater disposal systems or the like), objects (for example, trash cans, toilets or the like), animals (for example, contaminated livestock or the like), or the human body (for example, oral, diabetic foot or the like) to prevent proliferation of odor-causing microorganisms.

The composition for preventing odors according to the present disclosure may further include a variety of culture medium ingredients well-known in the art to improve the ability to form a biofilm depending on the coated substrate. The medium in the composition may suitably include, but not be limited to, agar, gelatin, alginate, carrageenan or pectin medium. Preferably, the medium may include PTYG, R2A or LB medium when the coating composition is applied to the evaporator core in the air conditioning system.

In addition, the composition for preventing odors according to the present disclosure may further include a fragrance, disinfectant or antimicrobial agent, in addition to the odorless microorganism, in order to block offensive odors or prevent or remove odor-causing bacteria.

In a preferred embodiment of the present disclosure, the composition of the present disclosure is to prevent emission of odors from an air conditioning system.

The air conditioning systems where the composition of the present disclosure is applied may include a system which can be installed in buildings, vehicles, trains, ships, aircraft and the like, and may be used to control the temperature, humidity, airflow or cleanliness of the air.

The substrate may be coated with the biofilm of the present disclosure. The substrate may suitably include an extruder, a blower, an evaporator core or the like in the air conditioning system, and in particular. Preferably, the biofilm of the present disclosure may be coated on an evaporator core.

The surface of the evaporator core in the air conditioning system may provide an environment which is suitable for growth and proliferation of bacteria due to condensation of condensate water derived from heat exchange of air. After a predetermined time, the attached bacteria may create a biofilm and survive as stable communities, which may be hard to remove. In other words, the odorless microorganisms may proliferate dominantly prior to microorganisms producing odor, thereby prevent proliferation of the odor producing microorganisms.

For instance, when the air conditioning system or the evaporator core is primarily or previously coated with dominant strains or odorless microorganisms with excellent viability, a biofilm may be formed in the evaporator core only with communities of those odorless microorganisms, and deposition and proliferation of odors and odor-inducing microorganisms may be significantly inhibited (Examples 8 and 9).

Meanwhile, as used herein, the term "odorless" used in relation to terms such as odorless microorganisms means a condition in which a subject cannot perceive anything by the olfactory organ. The criterion of odorlessness is also shown in the odor process test method (Notice No. 2007-17, National Institute of Environmental Research).

In another aspect, the present disclosure provides an evaporator core coated with the composition for preventing odors and a method of manufacturing the same.

The fin of the evaporator core may be made of aluminum or an aluminum alloy and the evaporator core may be produced using antibacterial-treated aluminum or a non-antibacterial-treated alloy material. The material for the evaporator core may not be limited to aluminum or an aluminum alloy and a metal with excellent thermal conductivity and superior corrosion resistance such as copper, may be used as the material. In an electric car or the like, a heat exchanger may be connected to a Peltier element and any material having a structure similar to or the same as the structure facilitating heat exchange may be used.

The method of coating the evaporator core with the composition for preventing odors containing the odorless microorganisms or a culture solution thereof may be selected from a method well-known in the art (for example, spraying, application or immersion). For example, the evaporator core may be immersed in a culture solution of the odorless microorganism to allow the fins in the evaporator core to be coated, so as to uniformly and thoroughly coat the entire surface of the evaporator core. The coating may be carried out at least once, at least two times or at least three times.

The culture solution of the odorless microorganism may be a microorganism culture solution having an optical density (O.D.) of about 0.3 to 0.9, or particularly of about 0.4 to 0.8.

When a microorganism culture solution having O.D. of about 0.3 to 0.9 is used, the concentration of the adhered microorganism may be of about $10^4$ cfu/g to $10^8$ cfu/g. When a microorganism culture solution having O.D. of about 0.4 to 0.8 is used, the concentration of the adhered microorganism may be of about $10^5$ cfu/g to $10^7$ cfu/g. When taking into consideration the fact that the concentration of microorganisms present in the evaporator core in a second-hand car is about $10^6$ cfu/g, in terms of application of vehicles, the microorganisms may be attached on the substrate at a concentration of $10^5$ cfu/g to $10^7$ cfu/g using a microorganism culture solution having O.D. of about 0.4 to 0.8.

The odorless microorganism coated by the method described above may be uniformly distributed and grown on the surface of the evaporator core and may form a biofilm stabilized thereon for a long time (30 days or longer) (Example 9).

In another aspect, the present disclosure provides a method of preventing odors in an air conditioner, including coating an evaporator core with the composition for preventing odors.

Accordingly, when forming a biofilm by coating with the composition for preventing odors containing odorless microorganisms or a combination thereof according to the present disclosure, permeation and growth of exterior microorganisms which may cause odors can be significantly prevented and the odors of the air conditioning system may be effectively prevented.

In another aspect, the present disclosure provides a method of detecting odors in an air conditioner including coating an evaporator core with the composition for preventing odors.

Whether the microorganisms included in the composition for preventing odors emit odors may depend on ingredients of nutrients that these microorganisms feed on and metabolize. It may be important that an odor is not generated, although the nutrient source of the actual industry to which the microorganisms are applied is fed or supplied.

In the case of an air conditioning system, microorganisms may metabolize various indoor or outdoor materials present in the air, as nutrients, and indoor or outdoor air pollutants or exhaust ingredients (petroleum such as gasoline, light oil or LPG) become nutrient sources of these microorganisms. Whether the air conditioning system emits odors may be previously detected when these nutrient sources are fed into the evaporator core coated with the microorganisms and applied to the industry.

In another aspect, the present disclosure provides, as microorganisms for coating an evaporator core to prevent odors in an air conditioning system, *Caulobacter vibrioides* HKMC-14 (Accession number: KCCM 11685P), *Bradyrhizobium diazoefficiens* HKMC-15 (Accession number: KCCM 11686P), *Bradyrhizobium daqingense* HKMC-16 (Accession number: KCCM 11687P), and *Methylobacterium brachiatum* HKMC-17 (Accession number: KCCM 11688P). The microorganisms may be used or coated alone or as a combination thereof to coat an evaporator core, for example, by forming a biofilm, to prevent odors in an air conditioning system.

The present disclosure provides a composition for preventing odors containing at least one odorless microorganism selected from the group consisting of *Caulobacter vibrioides, Bradyrhizobium diazoefficiens, Bradyrhizobium daqingense*, and *Methylobacterium brachiatum*, or a culture solution thereof. In addition, the present disclosure provides an evaporator core coated with the composition for preventing odors and a method of manufacturing the same. Furthermore, the present disclosure provides a method of manufacturing an odorless evaporator core not generating odors in an air conditioner, including coating an evaporator core with the composition for preventing odors.

Moreover, when forming a biofilm by coating a substrate on which odor-causing microorganisms may be grown with the composition for preventing odors, permeation and growth of exterior microorganisms causing odors may be significantly prevented and odors can be effectively prevented.

EXAMPLES

Hereinafter, the present disclosure will be described in more detail with reference to examples. These examples are provided only for illustration of the present disclosure and it would be obvious to those skilled in the art that the scope of the present disclosure is not limited by the examples depending on the subject matter of the present disclosure.

Example 1

Establishment of Odorous Long-Distance Taxi

The present inventors obtained five odorous long-distance taxis (TABLE 1), separated evaporator cores mounted on A to E vehicle models and sampled evaporator core specimens.

TABLE 1

| No. | Long-distance vehicle | Mileage (km) |
|---|---|---|
| 1 | Vehicle model A | 753,300 |
| 2 | Vehicle model B | 760,000 |
| 3 | Vehicle model C | 770,000 |
| 4 | vehicle model D | 857600 |
| 5 | Vehicle model E | 482800 |

Example 2

Evaporator Core Specimen Sampling

The evaporator core samples acquired from commercial taxis A to E, which had run for long time, were sealed in a polyethylene bag and refrigerated at a temperature of 4° C. before use. In order to isolate and culture microorganisms, 5 g of the fin specimens were collected from any spots including front and back parts in respective evaporator cores using a sterilized long nose plier and then mixed before use.

Example 3

Separation of Microorganisms from Evaporator Core

The microorganisms were separated from the evaporator cores in accordance with the following process and method.

① Specimens extracted from the evaporator cores were mixed and fed into a mixer.
② Sterilized 1×phosphate buffed saline (PBS) was fed into a 200 ml mixer.
③ The mixed specimen was mixed with PBS for 30 seconds.
④ The mixer was placed on ice for one minute.
⑤ Steps ③ and ④ were repeated twice.
⑥ The suspension was centrifuged at a temperature of 4° C. and 13,000 rpm for 3 minutes.
⑦ Only the supernatant was collected and transferred to a new tube.
⑧ The sterilized swab was soaked with the supernatant and the surface of the evaporator core, from which the sample was collected, was cleaned with the swab several times.
⑨ Only the head of the cleaned swab was immersed in the supernatant and vortexing was conducted.
⑩ The precipitate obtained in step ⑥ was mixed with the mixture of step ⑨ and the resulting mixture was used as an inoculation stock.

After steps ① to ⑩, microorganisms were separated by physical detachment from evaporator cores mounted on vehicle models A to E.

Example 4

Separate Culture of Microorganisms

The separation of bacteria from the air conditioner is generally carried out by performing heterotrophic plate culture on aerobic heterotrophic bacteria which are called general bacteria. Two complex nutrient media generally used for separation of bacteria are a PTYG agar medium and a R2A agar medium. In the case of PTYG agar medium, peptone 0.25 g (Difco), triptone 0.25 g (Difco), yeast extract 0.5 g (Difco), glucose 0.5 g (Difco), $MgSO_4$ 30 mg (Sigma), $CaCl_2$ 3 mg (Sigma), and Bactoagar 15 g (Difco) were added to 980 ml of distilled water, pH was adjusted to 7.0 and the resulting mixture was autoclaved at 121° C. for 15 minutes. In the case of R2A agar medium, yeast extract 0.5 g (Difco), proteose peptone No. 3 0.5 g (Difco), casamino acids 0.5 g (Difco), dextrose 0.5 g (Difco), soluble starch 0.5 g (Difco), sodium pyruvate 0.3 g (Difco), dipotassium sulfate 0.3 g (Difco), magnesium sulfate 0.05 g (Difco), and bacto agar 15 g (Difco) were added to distilled water 980 ml, pH was adjusted to 7.2 and the resulting mixture was autoclaved at a temperature of 121° C. for 15 minutes. Three kinds of antibiotics were used to isolate non-dominant general bacteria (TABLE 2) and the antibiotics were inoculated at a concentration of 100 ppm when the medium temperature reached to a temperature of 50° C. after sterilization of the filter, to produce antibiotic media.

TABLE 2

| No. | Antibiotic | Genus | Manufacturer |
|---|---|---|---|
| 1 | Kanamycin | Aminoglycoside | Sigma |
| 2 | Ampicillin | beta-lactam | Sigma |
| 3 | Chloramphenicol | Chloramphenicol | Sigma |

Example 5

Separate Culture of Dominant Strains in Entire Medium in which Evaporator Core Microorganisms are Cultured To separately culture dominant strains, first, various dominant strains should be selected through morphological approach of dilution ratio, and color, size and shape of colonies and the like. Accordingly, dominants strains were separately cultured in accordance with the following process.

① Bacteria were isolated from the separately cultured medium.
② A variety of bacteria having different morphologies were inoculated in a complex medium using a loop and purely isolated.
③ The medium which was grown the most was selected from seeded media and passage culture was conducted.

Example 6

Analysis of Genetic Characteristics of Evaporator Core Dominant Bacteria

Investigation of Fingerprints Through REP-PCR Pattern Analysis

REP-PCR is a molecular biological method of analyzing the structure of bacterial chromosomes and is a fingerprinting method which is capable of distinguishing specific bacterial strains from other bacteria. Genetic characteristics were analyzed in accordance with respective processes to conduct REP-PCR.

(1) Cell Lysis Process
① 2.5 µl of LYSE-N-GO PCR Reagent (Thermo Scientific) was placed in a PCR tube.

② Colonies were harvested with a pipette at a clean bench, placed in the tube and pipetting was conducted. The amount of colonies harvested should be determined not to make the solution slightly hazy.

③ According to manufacturer's instructions, culture was conducted in a PCR machine.

④ Cycles of lysis program listed in the following TABLE 3 were repeated and the PCR machine was allowed to stand at 80° C. during the cycles.

TABLE 3

| Cycle | Temperature(° C.) | Time(seconds) |
|---|---|---|
| 1 | 65 | 30 |
| 2 | 8 | 30 |
| 3 | 65 | 90 |
| 4 | 97 | 180 |
| 5 | 8 | 60 |
| 6 | 65 | 180 |
| 7 | 97 | 60 |
| 8 | 65 | 60 |
| 9 | 80 | hold |

(2) PCR Reaction

Suitable amounts of ingredients required for PCR reaction described in the following TABLE 4 were mixed to prepare a reaction mixture and, as shown in TABLE 5, pre-denaturation at a temperature of 94° C. for 7 minutes, denaturation at a temperature of 92° C. for 1 minute, annealing at a temperature of 51.5° C. for 1 minute, and extension at a temperature of 65° C. for 8 minutes were conducted, and denaturation, annealing and extension processes were repeated 33 times to conduct PCR amplification.

TABLE 4

| | | |
|---|---|---|
| ① | dNTP (2.5 mM each) | 12.5 μl |
| T② | Gitschier buffer | 5.0 μl |
| ③ | DMSO (100%) | 2.5 μl |

TABLE 5

| step 1 | 93° C. | 7 min |
|---|---|---|
| step 2 | 92° C. | 1 min |
| step 3 | 51.5° C. | 1 min |
| step 4 | 65° C. | 8 min |
| step 2, 3, 4: additional 33 cycles | | |
| step 6 | 65° C. | 16 min |
| step 7 | 4° C. | |

(3) Gel Electrophoresis

The DNA fragments amplified by PCR were collected, 1.2-1.5% agarose gel supplemented with EtBr was used, and a mixture of 6× dye and a sample in a ratio of 1 to 5 was loaded in an amount as much as possible. Since most PCR products were between 100 and 1,000 bp, they were loaded with a 100 bp ladder, and electrophoresis was conducted as slow as possible such that the middle (50 V) of bromophenol blue and xylene cyanol dyes reached the middle of the entire gel. Strains that have identical DNA patterns on gel are considered to be the same strains.

(4) Identification of Air Conditioner Dominant Bacteria Through 16S rRNA Genetic Analysis 16S rRNA (ribosomal ribonucleic acid) genes are used for identification of genetic classes of bacteria and can be identified at the level of genus and species of bacteria classified by REP-PCR. 16S rRNAs are RNAs which interact with various proteins to constitute ribosomes. Since complete sequences of 16S rRNAs or base sequences of the oligonucleotide list were found in 2,000 or more kinds of bacteria, bacteria can be classified into several main groups, based on gene similarity of 16S rRNAs. The degree of 16S rRNA base sequence similarity is considered to reflect phylogenetic distance between organisms, since variation of the 16S rRNA gene base sequence is much less than that of other gene base sequences present in most genomes. The method which analyzes base sequences of 16S rRNA gene fragments and identifies microorganisms depending on similarity thereof has been used as a representative method of identifying microorganisms, in particular, industrially useful microorganisms, in addition to the aforementioned fatty acid analysis and carbohydrate assimilation ability analysis.

16S rRNA PCR

PCR conditions (Total 50 μl): ingredients for the solution excluding DNAs and Taq were mixed in predetermined amounts as shown in the following TABLE 6 and the resulting mixture was added to 44.5 μl of a lysis solution. Then, as shown in the following TABLE 7, pre-denaturation at a temperature of 94° C. for 5 minutes, denaturation at a temperature of 94° C. for 1 minute, annealing at a temperature of 55° C. for 1 minute, and extension at a temperature of 72° C. for 1 min 30 seconds were conducted, and denaturation, annealing and extension steps were conducted 29 times to perform PCR amplification.

TABLE 6

| Autoclaved 3° D.W. | 22 μl |
|---|---|
| 10 × buffer (Roche) | 5 μl |
| dNTP (Roche, 2.5 mM) | 5 μl |
| DMSO | 5 μl |
| BSA (10 mg/ml) | 2.5 μl |
| 27 mf (20 pmole/μl) | 2.5 μl |
| 1492 r (20 pmole/μl) | 2.5 μl |
| DNA | 5 μl |
| Taq (Roche) | 0.5 μl |

TABLE 7

| step 1 | 94° C. | 5 min |
|---|---|---|
| step 2 | 94° C. | 1 min |
| step 3 | 55° C. | 1 min |
| step 4 | 72° C. | 1 min 30 sec |
| Go to step 2: additional 29 cycles | | |
| step 6 | 72° C. | 10 min |
| step 7 | 4° C. | hold |

5) PCR Purification

The products amplified by 16S-rRNA PCR were purified using a QIAQUICK PCR purification kit (Qiagen) in accordance with the following process.

① 5× volume of PB buffer of the PCR product was added.

② The mixed solution was seeded on a QIAquick column.

③ For binding of DNAs, centrifugation was conducted for one minute and the supernatant was removed.

④ For washing, 750 μl of PE buffer was placed in a QIAquick column, centrifugation was conducted for one minute and the supernatant was removed.

⑤ Centrifugation was conducted again for one minute.

⑥ The QIAquick column was transferred to a new tube.

⑦ In order to extract DNAs, 30 μl of EB buffer was added thereto and was allowed to stand for one minute.

⑧ Centrifugation was conducted for one minute to allow DNAs dissolved in EB to be collected in the tube.

(6) Names and Characteristics of Isolated Respective Microorganisms

<Microorganism 1>
1. Name of microorganism: HKMC-14
Generic name: *Caulobacter*
Specific name: *Vibrioides*
Accession number: KCCM 11685P (2015 Apr. 17)
Depository: Korean Culture Center of Microorganisms
Depository Address: Yurim B/D
25, Hongje-2-ga gil, Seodaemun-gu
SEOUL, 120-861
Republic of Korea
2. Remediation conditions
A. Remediation agent
(1) Composition: PTYG media (per 1 L, Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: 121° C. for 20 minutes
B. Temperature (° C.): cultured at 28° C. for 7 days
3. Medium
(1) Composition: PTYG media (per 1 L, Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: 121° C., 20 minutes
4. Culture conditions
A. Aerobic or anaerobic: aerobic
B. Temperature: 28° C.
C. Both shaking and standing (liquid, solid) are possible
5. Storage conditions
Temperature (° C.): −70° C.

<Microorganism 2>
1. Name of microorganism: HKMC-15
Generic name: *Bradyrhizobium*
Specific name: *Diazoefficiens*
Accession number: KCCM 11686P (2015 Apr. 17)
Depository: Korean Culture Center of Microorganisms
Depository Address: Yurim B/D
25, Hongje-2-ga gil, Seodaemun-gu
SEOUL, 120-861
Republic of Korea
2. Remediation conditions
A. Remediation agent
(1) Composition: PTYG media (per 1 L, Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: at 121° C. for 20 Minutes
B. Temperature (° C.): cultured at 28° C. for 7 days
3. Medium
(1) Composition: PTYG media (per 1 L Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: 121° C. for 20 minutes
4. Culture conditions
A. Aerobic or anaerobic: aerobic
B. Temperature: 28° C.
C. Both shaking and standing (liquid, solid) are possible
5. Storage conditions
Temperature (° C.): −70° C.

<Microorganism 3>
1. Name of microorganism: HKMC-16
Generic name: *Bradyrhizobium*
Specific name: *Daqingense*
Accession number: KCCM 11687P (2015 Apr. 17)
Depository: Korean Culture Center of Microorganisms
Depository Address: Yurim B/D
25, Hongje-2-ga gil, Seodaemun-gu
SEOUL, 120-861
Republic of Korea
2. Remediation conditions
A. Remediation agent
(1) Composition: PTYG media (per 1 L, Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: 121° C. for 20 minutes
B. Temperature (° C.): cultured at 28° C. for 7 days
3. Medium
(1) Composition: PTYG media (per 1 L Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: 121° C. for 20 minutes
4. Culture conditions
A. Aerobic or anaerobic: aerobic
B. Temperature: 28° C.
C. Both shaking and standing (liquid, solid) are possible
5. Storage conditions
Temperature (° C.): −70° C.

<Microorganism 4>
1. Name of microorganism: HKMC-17
Generic name: *Methylobacterium*
Specific name: *Brachiatum*
Accession number: KCCM 11688P (2015 Apr. 17)
Depository: Korean Culture Center of Microorganisms
Depository Address: Yurim B/D
25, Hongje-2-ga gil, Seodaemun-gu
SEOUL, 120-861
Republic of Korea
2. Remediation conditions
A. Remediation agent
(1) Composition: PTYG media (per 1 L, Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: 121° C. for 20 minutes
B. Temperature (° C.): 28° C. for 7 days
3. Medium
(1) Composition: PTYG media (per 1 L Peptone 0.25 g, Triptome 0.25 g, Yeast extract 0.5 g, Glucose 0.5 g, $MgSO_4$ 30 mg, $CaCl_2$ 3 mg) or R2A medium.
(2) pH: 7.0
(3) Sterilization conditions: 121° C. for 20 minutes
4. Culture conditions
A. Aerobic or anaerobic: aerobic
B. Temperature: 28° C.
C. Both shaking and standing (liquid, solid) are possible
5. Storage conditions
Temperature (° C.): −70° C.

Example 7

Sensory Evaluation of Isolated Microorganisms in Aluminum Fin (1) Culture in Nutrient Medium
For sensory evaluation of 26 kinds of microorganisms identified from Example 6, the microorganisms were cultured at a temperature of 28° C. in a nutrient medium from which microorganisms were isolated for 7 days. The process of culturing bacteria in a nutrient medium are described as follows.

① Pure separately cultured microorganisms were inoculated in a liquid nutrient medium.

② The inoculated medium was cultured at a temperature of 28° C. for 5 to 7 days.

③ 100 μL of the bacteria cultured in the liquid medium was inoculated in a solid nutrient medium.

④ The inoculated bacteria was evenly spread using a spreader.

⑤ A petri dish was sealed and cultured at a temperature of 28° C. for 10 days.

(2) Sensory Evaluation in Aluminum Fin in 26 Species of Dominant Microorganisms Isolated from Long-Distance Taxi Microorganisms A rectangular aluminum fin was sterilized and dipped in dust and nutrient media. Then, bacteria were inoculated into and cultured in the nutrient medium under the conditions described in ② to ④ and evaluated. Sensory evaluation results are shown in the following TABLE 8 (primary) and TABLE 9 (secondary). Primary and secondary sensory evaluation were conducted depending on difference in microorganism growth rate.

Antimicrobial-treated aluminum fin: aluminum, which is a main ingredient of the evaporator core, is antibacterial-coated. Coating of the evaporator core finished product which is mass-produced and commercially available.

TABLE 8

| No. | Specific name | Panel 1 | Odor intensity | Panel 2 | Odor intensity | Panel 3 | Odor intensity | Selection of odorless microorganism |
|---|---|---|---|---|---|---|---|---|
| Control | Aluminum fin | Odorless | 0 | Odorless | 0 | Odorless | 0 | |
| 1 | *Chryseobacterium geocarposphaerae* | Salty smell | 3.5 | Salty smell | 3 | Salty smell, stink | 2.9 | X |
| 2 | *Spirosoma panaciterrae* | Salty smell | 2 | Water smell | 1 | Metallic (iron) Odor | 2 | X |
| 3 | *Spirosoma linguale* | Salty smell | 3 | Cabbage, salty smell | 2.5 | Stink, salty smell | 3.5 | X |
| 4 | *Sphingomonas asaccharolytica* | Fishy smell | 1 | Water smell | 1 | Salty smell, stink | 2.3 | X |
| 5 | *Bradyrhizobium diazoefficiens* | Fishy smell | 1.5 | Odorless | 0.5 | Odorless | 0 | ○ |
| 6 | *Methylobacterium brachiatum* | Odorless | 0 | Weak salty smell | 1.5 | Metallic (iron) odor | 1.2 | ○ |
| 7 | *Methylobacterium longum* | Acidic smell | 0.5 | Salty smell, fishy smell | 2.5 | Alcohol, stink | 3.2 | X |
| 8 | *Bradyrhizobium daqingense* | Odorless | 0 | Water smell | 1 | Metallic (iron) odor | 1 | ○ |
| 9 | *Radyrhizobium liaoningense* | Plastic | 1.5 | Soil smell | 1.5 | Metallic (iron) odor | 1.3 | X |
| 10 | *Methylobacterium radiotolerans* | Stench of urine | 2 | Vinegar scent | 2 | Sweet smell | 1 | X |
| 11 | *Methylobacterium variabile* | Chemical smell | 2 | Salty smell, fishy smell | 2 | Chicken coop | 1.5 | X |
| 12 | *Caulobacter vibrioides* | Odorless | 1 | Odorless | 0 | Odorless | 0 | 0 |

TABLE 9

| No. | Specific name | Panel 1 | Odor intensity | Panel 2 | Odor intensity | Panel 3 | Odor intensity | Panel 4 | Odor intensity | Selection of odorless microorganism |
|---|---|---|---|---|---|---|---|---|---|---|
| Control | Aluminum fin | Odorless | 0 | Odorless | 0 | Odorless | 0 | Odorless | 0 | |
| 1 | *Sphingomonas glacialis* | Odorless | 1 | Odorless | 0 | Odorless | 0 | Odorless | 0 | ○ |
| 2 | *Phingomonas aquatilis* | Unpleasant smell | 2.5 | Chicken feces | 1.5 | Dust | 1 | Chicken smell, salty smell | 0.5 | X |
| 3 | *Sphingomonas mucosissima* | Chicken smell | 2 | Smell of egg | 1.8 | Fishy smell | 1.5 | Chicken feathers | 0.6 | X |
| 4 | *Methylobacterium tarhaniae* | Chicken smell | 2.3 | Chemical smell | 2.5 | Fishy smell | 2.5 | Chicken feathers | 0.6 | X |

TABLE 9-continued

| No. | Specific name | Panel 1 | Odor intensity | Panel 2 | Odor intensity | Panel 3 | Odor intensity | Panel 4 | Odor intensity | Selection of odorless microorganism |
|---|---|---|---|---|---|---|---|---|---|---|
| 5 | *Sphingomonas melonis* | Chicken smell | 2.1 | Chemical smell | 2 | Water smell, fishy smell | 2 | Chicken smell | 0.8 | X |
| 6 | *Acidovorax avenae* | Odorless | 0.3 | Smell of trash can | 1.5 | Almost no | 0.5 | Medium, bitter smell | 1.2 | X |
| 7 | *Acidovorax oryzae* | Presence of initial smell | 2 | Smell of egg | 2 | Salty smell | 1 | Goose feathers | 1.3 | X |
| 8 | *Sphingomonas ginsenosidi mutans* | Chicken smell | 2.6 | Plastic smell | 2.5 | Fishy smell, smell of old book | 2.5 | Stink | 1.5 | X |
| 9 | *Sphingomonas dokdonensi* | Medium | 2.3 | Fishy smell | 1.5 | Fishy smell | 1.5 | Stench of urine | 1.8 | X |
| 10 | *Pelomonas puraquae* | Fecal odor | 3 | Stench of urine | 2 | Smell of decayed food | 3.2 | Stench of urine | 2.2 | X |
| 11 | *Methylobacterium platani* | Unpleasant pungent smell | 2.5 | Sour, old plastic smell | 2.5 | Sour, factory smell | 2.8 | Sour smell | 2.5 | X |
| 12 | *Methylobacterium tardum* | Fecal odor | 2.5 | Stench of urine | 3 | Fishy smell, water smell | 3 | Acidic smell | 3 | X |
| 13 | *Spirosoma radiotolerans* | Medium, chicken fecal | 3 | Stench of urine, acidic smell | 3 | Fishy smell, smell of wet towel | 3.5 | Stench of urine | 3.2 | X |
| 14 | *Fibrella aestuarina* | Fecal smell | 3.5 | Stench of urine, acidic smell | 4 | Odor of toilet | 4 | Acidic smell, stench of urine | 4 | X |

As a result of inoculation and culture of the 26 species of microorganisms in aluminum antimicrobial fin, the following four kinds of microorganisms were odorless.

TABLE 10

| No. | Antimicrobial fin | Generic name |
|---|---|---|
| 1 | Odorless | *Bradyrhizobium diazoefficiens* |
| 2 | Odorless | *Methylobacterium brachiatum* |
| 3 | Odorless | *Bradyrhizobium daqingense* |
| 4 | Odorless | *Caulobacter vibrioides* |

As used herein, the term "odorless" means a condition in which a substrate does not perceive anything by the olfactory organ.

In relation to evaluation of odors, sensory evaluation was conducted using an olfactory organ in accordance with the current provision. Other odor evaluation methods excluding olfactory evaluation do not exist all over the world. As can be seen from the aforementioned example, the criterion of "odorless" is decided depending on the criterion on which human perceive with the olfactory organ by a sensory evaluation method.

The criterion to determine odorlessness is shown in the odor process test method (Notice No. 2007-17, National Institute of Environmental Research). On page 65 of the odor process test method, it is stated that the term "odorless" means a condition in which a subject cannot detect anything by the olfactory organ.

Furthermore, as described on pages 65 and 66 of the odor process test method also defining the criterion to select people who can evaluate an odor, the determination criterion is considered to be clearer.

In addition, it can be seen that "odorless" is written in the part corresponding to "0" in the grade table on page 2, Chapter 2, and Regulation Article 4 of the Regulatory Standards.

As such, the criterion of "odorless" in sensory evaluation means a condition in which a subject selected by a predetermined criterion cannot perceive anything by olfaction, as is clearly defined in Korean and Japanese regulations.

Example 8

Evaluation of Optimal Adhesion Conditions of Odorless Microorganisms (1) Analysis of Optimal Fin Adhesion Concentration of Odorless Microorganisms In order to coat the evaporator core with 11 species of odorless microorganisms, an optimal adhesion concentration to inoculate at a level of $10^6$ cfu/g was determined, as shown in the research result in 2012 (priority application). Concentration determination test was conducted using *Methylobacterium aquaticum* which is one of common strains, *Methylobacterium aquaticum* was cultured at 28° C. until the late log phase, washed with sterilized 0.85% saline and then cultured at a temperature of 4° C. for 18 hours. After culture at a temperature of 4° C., optical density (O.D.) was adjusted to 0.749, 0.588, 0.55, 0.5 and 0.45, and 2 g of a U-shaped fin was dipped and adhered while shaking at room temperature and at a predetermined rate (rpm) for one hour. The fin to which each concentration of microorganism was adhered was detached using a mixer and spread-plated on the R2A agar plate by serial dilution.

As a result of spread plating, it could be seen that the concentration of microorganisms adhered to the fin changes depending on the value of O.D. When O.D. was 0.749, the level of microorganisms adhered to the fin was $1.53\times10^8\pm1.52\times10^7$ cfu/g fin, and when O.D. was 0.588 and 0.55, the levels of microorganisms adhered to the fin were $4.00\times10^7\pm1.00\times10^7$ cfu/g fin, and $1.03\times10^7 8.50\times10^5$ cfu/g fin, respectively. In addition, at O.D. of 0.5 and 0.45, the levels of microorganisms adhered to the fin were $6.00\times10^6 7.00\times10^5$ cfu/g fin, and $2.53\times10^6\pm3.51\times10^5$ cfu/g fin, respectively, which indicates that the adhesion degree was proportional to O.D. Ten different species of odorless microorganisms were coated at 0.5 which is the O.D value which allows for coating $10^6$ cfu/g of microorganisms present in the evaporator core, from which the microorganisms were isolated, among these adhesion concentrations.

(2) Confirmation of Adhesion of Odorless Microorganisms to Evaporator Core and Fin As a result of the fin adhesion test, regardless of genus, 11 kinds of odorless microorganisms exhibited an identical adhesion degree at a predetermined O.D. value. Accordingly, the amount of microorganisms adhered to the evaporator core was checked using a culture solution having the same O.D. as the fin with *Methylobacterium aquaticum* which is one strain.

The amount of *Methylobacterium aquaticum* adhered to the evaporator core adjusted to O.D. of 0.5 was $8.95\times10^6\pm5.51\times10^5$ cfu/g fin. The evaporator core adhered using the same culture solution exhibited an adhesion degree of $2.55\times10^6\pm3.51\times10^5$ cfu/g fin. This result indicates that the same level of microorganisms was adhered when using the culture solution having the same O.D.

Example 9

Evaluation of 30-Day Survival of Four Combinations

Survival evaluation for 30 days was conducted on the following combinations. The combination number of microorganisms used for the coating combinations and the microorganism list thereof are given below (TABLE 11).

TABLE 11

| Combination | | |
|---|---|---|
| 1 | *Methylobacterium aquaticum* | PR1016A |
| 2 | *Caulobacter vibrioides* | TX0632 |
| 3 | *Methylobacterium brachiatum* | TX0642 |
| 4 | *Bradyrhizobium diazoefficiens* | TX0618 |

To evaluate 30-day short-term effects of odorless microorganism combinations isolated from taxis, the combinations were organized and 30-day short-term evaluation was conducted on the combinations.

The combination consisting of four strains of *Methylobacterium aquaticum* PR1016A, *Caulobacter vibrioides* TX0632, *Methylobacterium brachiatum* TX0642, and *Bradyrhizobium diazoefficiens* TX0618 was detected at time of 0 in a total level of $3.99\times10^6\pm2.82\times10^6$ cfu/g fin, and red and white colonies were detected at levels of $3.62\times10^6\pm2.79\times10^6$ cfu/g fin and $3.67\times10^5\pm3.06\times10^4$ cfu/g fin, respectively. After 30 days, the white colony was not detected and the red colony was detected in a level of $2.14\times10^6\pm1.25\times10^5$ cfu/g fin, which was equal to that of the total bacteria number (FIG. 2).

As a result of counting the number of microorganisms by REP-PCR, in the case of the combination at time 0, out of 111 representative samples, 43 samples were detected to be *Methylobacterium aquaticum* PR1016A, 6 samples were detected to be *Caulobacter vibrioides* TX0632, 52 samples were detected to be *Methylobacterium brachiatum* TX0642, and 10 samples were detected to be *Bradyrhizobium diazoefficiens* TX0618. These results showed that two species of *Methylobacterium* sp. 2 occupied 85.6% of the combination (FIG. 3).

After 30 days, analysis results of REP-PCR pattern showed that, out of 89 representative samples, 26 *Methylobacterium aquaticum* PR1016A samples were detected to survive, and 63 *Methylobacterium brachiatum* TX0642 samples were detected to survive, which means that *Methylobacterium* sp. was dominant under the evaporator core environment, regardless of the passage of time.

In addition, growth of outer microorganisms was not observed.

In conclusion, to evaluate 30-day short-term effects of the odorless microorganism combinations isolated from the taxi, the combinations were organized, and *Methylobacterium aquaticum* PR1016A and *Methylobacterium brachiatum* TX0642 were detected to survive after 30 days. The biofilms made of these two species were kept odorless and inhibited growth of exterior microorganisms.

Although the preferred embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed:

1. An evaporator core coated with a coating composition for preventing odors, the coating composition comprising at least one odorless microorganism selected from the group consisting of *Caulobacter vibrioides* HKMC-14 (Accession number: KCCM 11685P), *Bradyrhizobium diazoefficiens* HKMC-15 (Accession number: KCCM 11686P), *Bradyrhizobium daqingense* HKMC-16 (Accession number: KCCM 11687P) and *Methylobacterium brachiatum* HKMC-17 (Accession number: KCCM 11688P), or a culture solution thereof.

2. The evaporator core of claim 1, wherein the microorganism is adhered to the evaporator core at a concentration of about $10^4$ cfu/g to $10^8$ cfu/g.

3. The evaporator core of claim 1, wherein the microorganism in the coating composition forms a biofilm on a surface of the evaporator core.

4. An air conditioning system comprising the evaporator core of claim 1.

5. A method of manufacturing an odorless evaporator core comprising coating an evaporator core with a coating composition for preventing odors, the coating composition comprising at least one odorless microorganism selected from the group consisting of *Caulobacter vibrioides* HKMC-14 (Accession number: KCCM 11685P), *Bradyrhizobium diazoefficiens* HKMC-15 (Accession number: KCCM 11686P), *Bradyrhizobium daqingense* HKMC-16 (Accession number: KCCM 11687P), and *Methylobacterium brachiatum* HKMC-17 (Accession number: KCCM 11688P), or a culture solution thereof.

6. The method of claim 5, wherein the coating step comprises adhering microorganisms included in the composition at a concentration of about $10^4$ cfu/g to $10^8$ cfu/g to the evaporator core.

7. The method of claim 5, further comprising proliferating microorganisms in the coating composition to form a biofilm.

8. A method of preventing odors in an air conditioning system comprising coating an evaporator core with a coating composition for preventing odors, the coating composition comprising at least one odorless microorganism selected from the group consisting of *Caulobacter vibrioides* HKMC-14 (Accession number: KCCM 11685P), *Bradyrhizobium diazoefficiens* HKMC-15 (Accession number: KCCM 11086P), *Bradyrhizobium daqingense* HKMC-16 (Accession number: KCCM 11687P), and *Methylobacterium brachiatum* HKMC-17 (Accession number: KCCM 11688P), or a culture solution thereof.

9. The method of claim 8, wherein the coating step comprises adhering microorganisms included in the composition at a concentration of about $10^4$ cfu/g to $10^8$ cfu/g to the evaporator core.

10. The method of claim 8, further comprising proliferating microorganisms in the coating composition to form a biofilm.

11. A method of detecting odors in an air conditioning system comprising:
coating the evaporator core with a coating composition for preventing odors, the coating composition comprising at least one odorless microorganism selected from the group consisting of *Caulobacter vibrioides* HKMC-14 (Accession number: KCCM 11685P), *Bradyrhizobium diazoefficiens* HKMC-15 (Accession number: KCCM 11686P), *Bradyrhizobium daqingense* HKMC-16 (Accession number: KCCM 11687P), and *Methylobacterium brachiatum* HKMC-17 (Accession number: KCCM 11688P), or a culture solution thereof;
feeding petroleum or an air contaminant serving as a nutrient source of microorganisms in the coating composition; and
detecting whether or not an odor is generated.

12. The method of claim 8, wherein the coating composition comprises *Caulobacter vibrioides* HKMC-14 (Accession number: KCCM 11685P) to prevent an odor in an air conditioning system.

13. The method of claim 8, wherein the coating composition comprises *Bradyrhizobium diazoefficiens* HKMC-15 (Accession number: KCCM 11686P) to prevent an odor in an air conditioning system.

14. The method of claim 8, wherein the coating composition comprises *Bradyrhizobium daqingense* HKMC-16 (Accession number: KCCM 11687P) to prevent an odor in an air conditioning system.

15. The method of claim 8, wherein the coating composition comprises *Methylobacterium brachiatum* HKMC-17 (Accession number: KCCM 11688P) to prevent an odor in an air conditioning system.

16. An air conditioning system coated with a coating composition for preventing odors comprising at least one odorless microorganism selected from the group consisting of *Caulobacter vibrioides* HKMC-14 (Accession number: KCCM 11685P), *Bradyrhizobium diazoefficiens* HKMC-15 (Accession number: KCCM 11686P), *Bradyrhizobium daqingense* HKMC-16 (Accession number: KCCM 11687P), and *Methylobacterium brachiatum* HKMC-17 (Accession number: KCCM 11688P), or a culture solution thereof.

* * * * *